US007803526B2

(12) United States Patent
Singh et al.

(10) Patent No.: US 7,803,526 B2
(45) Date of Patent: Sep. 28, 2010

(54) **DEVELOPMENT OF DIAGNOSTIC KIT FOR THE DETECTION OF *CHRYSANTHEMUM VIRUS* B**

(75) Inventors: Lakhmir Singh, Palampur (IN); Vipin Hallan, Palampur (IN); Aijaz Ashgar Zaidi, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/191,862

(22) Filed: Aug. 14, 2008

(65) Prior Publication Data

US 2009/0142747 A1 Jun. 4, 2009

Related U.S. Application Data

(60) Division of application No. 11/598,624, filed on Nov. 14, 2006, now abandoned, which is a continuation of application No. 11/369,717, filed on Mar. 8, 2006, now abandoned.

(30) Foreign Application Priority Data

Jul. 25, 2005 (IN) .................. 1982/DEL/2005

(51) Int. Cl.
*C12Q 1/70* (2006.01)
(52) U.S. Cl. .......................................... 435/5
(58) Field of Classification Search ............... None
See application file for complete search history.

(56) References Cited

OTHER PUBLICATIONS

Raisada et al (Indian Journal of Experimental Biology 27:1094-1096, 1989).*
Levay et al (Journal of General Virology 72:2333-2337, 1991).*
Ling et al (European Journal of Plant Pathology 106:301-309, 2000).*
Jelkmann et al (Journal of General Virology 71:1251-1258, 1990).*
Song et al (Molecules and Cells 7: 705-709, 1997).*
Choi et al (Agricultural Chemistry and Biochemistry 38:49-54, 1995).*
Hourani et al (Journal of Plant Pathology 85:197-204, 2003).*
Nickel et al (Fitopatologia Brasiliera 29:558-562, 2004).*
Rodoni et al (Archives of Virology 144:1725-1737, 1999).*
Abou-Jawdah et al (Journal of Virological Methods 121:31-38, 2004).*
Genbank Accession No. AJ 566195, Hallan et al., "Molecular characterization of the Indian Isolate of Chrysanthemum Virus B", Jun. 11, 2003, Floriculture Division, Inst. of Himalayn Bioresource Technology, PO Box 6, Palampur, HimaChal Pradesh; 176061, India, p. 1.
Genbank Accession No. AJ 566196, Hallan et al., "Molecular characterization of the Indian Isolate of Chrysanthemum Virus B," Jun. 11, 2003, Floriculture Division, Inst. of Himalayn Bioresource Technology, PO Box 6, Palampur, HimaChal Pradesh; 176061, India, p. 1.

* cited by examiner

*Primary Examiner*—Mary E Mosher
(74) *Attorney, Agent, or Firm*—Sughrue Mion, PLLC

(57) ABSTRACT

The present invention provides a method for detection of *Chrysanthemum virus* B in plants using desined primers of Sequence ID 1: Upstream primer TGCCTCCCAAACCG-GCACCAGGTGAT Sequence ID 2: Downstream primer: TTTATAATGTCTTATTATTCGCAT It also relates to a diagnostic kit useful for detection of coat protein of *Chrysanthemum virus* B in plants comprising: polyclonal antibodies against *Chrysanthemum virus* B coat protein in plants; conjugate labeled with alkaline phosphatase; coating buffer; extraction buffer; ECI buffer; PNP buffer.

9 Claims, No Drawings

DEVELOPMENT OF DIAGNOSTIC KIT FOR THE DETECTION OF *CHRYSANTHEMUM VIRUS* B

This is a divisional of application Ser. No. 11/598,624 filed Nov. 14, 2006, now abandoned which is a Continuation Application of U.S. application Ser. No. 11/369,717 filed Mar. 8, 2006 now abandoned. The entire disclosures of the prior applications, application Ser. Nos. 11/598,624 and 11/369,717 are hereby incorporated by reference.

FIELD OF INVENTION

The present invention relates to a primers useful for detection of *Chrysanthemum virus* B in plants.

More particularly this invention relates to a method for detection of Chrysanthemum virus B in plants by using a primers useful for detection of *Chrysanthemum virus* B in plants.

The present invention also relates to a diagnostic kit useful for detection of coat protein of *Chrysanthemum virus* B in plants.

BACKGROUND OF INVENTION

Chrysanthemum is one of the important cut flower worldwide. It ranks $3^{rd}$ in world among the cut flowers. Chrysanthemum is commonly propagated vegetatively and this practice allows the viruses, once established in the plants to be perpetuated from generation to generation. Quality of germplasm and minimizing the infection of the viruses to different cultivars, proper diagnosis and control for viral diseases are not only desirable but also essential for improving crop productivity.

*Chrysanthemum virus* B (CVB), a carlavirus has a narrow host range and distributed worldwide wherever Chrysanthemums are grown. It infects Chrysanthemum and about 10 other species in 5 dicotyledonous families (Brunt, A. A., Crabtree, K., Dallwitz, M. J., Gibbs, A. J., and Watson, L. (Edts) Viruses of Plants, CAB International, UK. Page No. 398-400). CVB is widespread throughout the country. During a survey of chrysanthemum cvs. all tested commercial stocks were found to show disease incidence ranging between 40% to 95% (Verma, N., Sharma, A., Ram, R., Hallan, V., Zaidi, A. A. and Garg, I. D. (2003) Detection, identification and incidence of Chrysanthemum B carlavirus in chrysanthemums in India. *Crop Prot.* 22, 425-429). At the Institute of Himalayan Bioresource Technology, Palampur chrysanthemum cultivars were collected from twenty eight geographical areas. Twenty eight isolates were cloned, sequenced and sequences were submitted to Genbank. Different primer pairs were designed (EMBL Nucleotide Sequence Accession Numbers: AJ566196, AJ566195, AJ609493, AJ609494, AJ609495, AJ609496, AJ609497, AJ609498, AJ609499, AJ609500) and used successfully for identification and characterization of an Indian isolates of CVB. This also shows wide spread occurrence of CVB in chrysanthemum being cultivated in different parts of country.

CVB was first reported from Netherlands as a member of carlavirus group (Noordam, D. 1952 Virusziekten bij chrysant in Nedeland. With a summary: virus disease of *Chrysanthemum morifolium* in Netherlands. *Tijdschrift over Plantenziekten*. 58, 121-190). CVB infection results in loss of flower quality, mild leaf mottling, vein clearing or a combination of these is found (Hollings, M. and Stone, O. M. (1972) *Chrysanthemum virus* B CMI/AAB Descriptions of Plant viruses No. 110). Symptoms ranging from mosaic, malformation and slight to severe necrosis have also been reported (Hakkart, F. A. and Matt, D. Z. (1974) Variation of *Chrysanthemum virus* B. J. Plant Path. 80, 97-103).

Traditional methods of diagnosis of plant viruses require bioassay through an indicator plant, symptom observation, host range determination, and particle morphology and vector relations. These processes are time consuming and require a lot of labour. However, progress in molecular biology, biochemistry and immunology has led to the development of new accurate, rapid and less labour-intensive methods of virus detection. There are various diagnostic techniques available in the field of viral diagnostics like precipitation tests, agglutination tests, fluorescent antibody test, enzyme linked immunosorbant assay, dot immunosorbant assay, tissue blotting assay, western blotting, nucleic acid hybridization with radio labeled and non radio-labeled probes and polymerase chain reaction based detection.

Immunological techniques have been successfully used for the detection of CVB from *Chrysanthemum morifolium* (Raizada, R. K., Srivastava, K. M., Chandra, G. and Singh, B. P. (1989) Comparative evaluation of sero-diagnostic methods for detection of *Chrysanthemum virus* B in chrysanthemum. *Indian J. Exp. Biol.* 27, 1094-1096). Serological methods were used effectively for diagnosis of *Chrysanthemum virus* B (Zaidi, A. A., Ram, R., Zaidi, S. N. H. and Mukherjee, D. (1990) Diagnosis of viruses in some ornamental plants with special reference to serological methods: New Developments. Indian Rev. Life Sci. 13, 157-174).

Enzyme linked immunosorbant assay (ELISA) and other modified form of ELISA have been extensively used for the detection of CVB from *Chrysanthemum morifolium* (Verma, N., Sharma, A., Ram, R., Hallan, V., Zaidi, A. A. and Garg, I. D. (2003) Detection, identification and incidence of Chrysanthemum B carlavirus in chrysanthemum in India. *Crop Prot.* 22, 425-429). It is highly effective in detecting the CVB from leaves. Using the DAS-ELISA, status of the viral disease was analyzed for 36 cultivars of *Chrysanthemum morifolium*. Some cultivars also exhibit mild leaf mottling, vein clearing or a combination of these (Hollings, M. and Stone, O. M. (1972) *Chrysanthemum virus* B CMI/AAB Descriptions of Plant viruses No. 110). Therefore, it is important to have reliable and quick diagnostics to diagnose the latent infection and for establishing the serological relationship between the isolates of the *Chrysanthemum virus* B. Similar to ELISA, Immunosorbant Electron Microscopy (ISEM) also revealed easy detection of CVB from leaves (Verma, N., Sharma, A., Ram, R., Hallan, V., Zaidi, A. A. and Garg, I. D. (2003) Detection, identification and incidence of Chrysanthemum B carlavirus in chrysanthemum in India. *Crop Prot.* 22, 425-429). Similar to ELISA, ISEM could detect the CVB from chrysanthemum leaves.

During last decade, RT-PCR has been used with varying degree of modification for detection of viral genome in infected plants (Yamamoto, H., Kiguchi, T. and Ohya, T. (2001) $52^{nd}$ Annual Report of the Society of Plant Protection of North Japan. 85-86). Partial sequence of the *Chrysanthemum virus* B has been worked out and it was 3.4 kb (Levay, K.

E. and Zavriev, S. K. (1991) Nucleotide sequence and gene organisation of the 3'-terminal region of *Chrysanthemum virus* B genomic RNA. *J. Gen. Virol.* 72(10), 2333-7). At IHBT, Palampur approximately 5 Kb of the CVB genome has been sequenced (EMBL Nucleotide Sequence Accession Numbers: AJ617281, AJ617282, AJ617287, AJ585240, AJ704627, AJ580956, AJ633542, AJ633540, and AJ633629). On the basis of sequencing of various geographical isolates, three biological isolates have been identified including the earlier reported Russian isolate, which resembles one of the three isolates.

OBJECTS OF THE INVENTION

The main object of the present invention is to provide primers useful for detection of *Chrysanthemum virus* B in plants.

Another object of the present invention is to provide a method for detection of *Chrysanthemum virus* B in plants by using designed primers useful for detection of *Chrysanthemum virus* B in plants.

Still another object of the present invention is to provide a diagnostic kit useful for detection of coat protein of *Chrysanthemum virus* B in plants.

SUMMARY OF THE INVENTION

The present invention relates to a method for detection of *Chrysanthemum virus* B in plants using desined primers of

```
Sequence ID 1: Upstream primer    ATGCCTCCCAAACCGGCACCAGGTGAT

Sequence ID 2: Downstream primer: TTTATAATGTCTTATTATTCGCAT
```

It also relates to a diagnostic kit useful for detection of coat protein of Chrysanthemum virus B in plants comprising:
a) polyclonal antibodies against *Chrysanthemum virus* B coat protein in plants;
b) conjugate labeled with alkaline phosphatase;
c) coating buffer;
d) extraction buffer;
e) ECI buffer;
f) PNP buffer;
g) Instruction manual.

DETAILED DESCRIPTION OF THE INVENTION

Specific sequence of CVB was detected in total RNA extract of infected plants by initially transcribing the viral RNA into cDNA and then amplifying by polymerase chain reaction. Like ELISA and ISEM, PCR also readily detects CVB in leaves. Thus DAS-ELISA, ISEM and RT-PCR are the suitable techniques to detect CVB infecting Chrysanthemum. RT-PCR and nucleic acid hybridization are sensitive tools to detect the virus but they require sophisticated instruments which are costly also. Till now ELISA have been used extensively used for diagnosis of virus infecting chrysanthemum and other plants, as these are quick, easy to perform, can be used even in field conditions and are cost effective. These can be exploited in the form of diagnostic kits. For the development of diagnostic kit coat protein gene of CVB submitted to EMBL data (Vide Accession No. AJ580956) was amplified using the especially designed primers having restriction enzyme sites compatible for directional and inframe cloning in pGex-2TK vector. Amplified product was cloned into pGex 2TK vector by transforming into BL21 competent cells.

Cloned coat protein gene was induced in transformed *E. coli* cells grown in YT medium. Expression conditions were standardized against IPTG concentration, time of incubation, growth conditions and method of cell disruption. Culture was induced using 0.25 mM isopropyl-β-D-thiogalactopyranoside (IPTG) final concentration at 0.5 $OD_{600}$ for 3 hrs at 25° C., along with disruption of cell using both lysozyme (10 mg/ml) and sonication (pulse on for 9.0 sec. and pulse off for 4 sec.) to give the maximum expressed recombinant coat protein yield in soluble form.

Expressed coat protein was purified to homogeneity by affinity chromatography on glutathione-agarose. Immobilization of glutathione on an agarose matrix makes a highly efficient affinity chromatography resin. Bound GST fusion proteins were readily displaced from the column by elution with buffer containing free glutathione.

Purified protein preparations obtained after affinity chromatography were used as antigen for immunization of rabbit (Meenu Katoch, A. A. Zaidi and Raja Ram. 2002. Development of diagnostic kit for the detection of Bean yellow mosaic virus. Patent file no 76/NF/2002). Healthy white New Zealander male albino rabbits approximately six months old were used to raise the hyperimmune sera against CVB. Antigen (about 100 μg per injection) was mixed with Freund's incomplete adjuvant (1:1) and was injected intramuscularly into thigh muscles of rabbits. Four injections were given at the interval of one week. After one week of immunization schedule, the animals were bled from the marginal ear vein. The blood was collected in a glass tube and allowed to clot at room temperature for one hour. Subsequently, the glass tube was kept at 4° C. overnight. The serum was centrifuged at 2000 rpm for ten minutes at 4° C. The supernatant was collected and stored at 4° C. after adding sodium azide to a concentration of 0.2% (w/v).

Accordingly the present invention Primers useful for detection of *Chrysanthemum virus* B (CVB) in plants, comprising the following sequence:

```
Sequence ID 1: Upstream primer    ATGCCTCCCAAACCGGCACCAGGTGAT

Sequence ID 2: Downstream primer  TTTATAATGTCTTATTATTCGCAT
```

Further, the present invention also provides a method for detection of Chrysanthemum virus B (CVB) in plants, wherein the said method comprising the steps of:
a) providing a purified coat protein of CVB by using designed primers of

```
Sequence ID 1: Upstream primer    ATGCCTCCCAAACCGGCACCAGGTGAT

Sequence ID 2: Downstream primer  TTTATAATGTCTTATTATTCGCAT
``` b) preparing polyclonal antibodies against CVB coat protein obtained from step (a);

c) performing direct antibody sandwich enzyme linked immunosorbent assay (DAS ELISA) for detection of CVB In an embodiment of the present invention, the complete coat protein of CVB is amplified using designed primers having a

```
Sequence ID 1: Upstream primer    ATGCCTCCCAAACCGGCACCAGGTGAT

Sequence ID 2: Downstream primer  TTTATAATGTCTTATTATTCGCAT
```

In another embodiment of the present invention, the complete coat protein of CVB comprising sequence ID having No.

```
CAI51623MPPKPAPGDNEGNASGSTPTPSPPHPARTAEEARLRLAEMEREREQEQSLE

EMNSNTPDDDARNISRLTQLAALLRREQTNVHVTNMALEIGRPALQPPPNMRGDPT

NMYSQVSTDFLWKIKPQRISNNMATSEDMVKIQVALEGLGVPTESVKEVIIRLVLNC

ANTSSSVYQDPKGVIEWDGGAIIADDVVGVINEHSTLRKVCRLYAAVAWNYMHLQ

QTPPSDWSAMGFHPNVKYAAFDFFDYVENGAAIGPSGGIVPKPTRAEYVAYNTYKM

LALNKANNNDTFGNFDSAITGGRQGPAIHNNLNNANNKTL is cloned in pGEX-2TK followed by transformation using E-coli strain BL 21.
```

Further in an embodiment of the present invention, the optimal expression of CVB coat protein is checked with 0.25-1 mM IPTG concentration at about temperature 25 degree C. for 3.5-4 h.

Still in an embodiment of the present invention, obtained coat protein of CVB is sequenced by known sequencing methods.

Still in an embodiment of the present invention, the purification of CVB coat protein is carried out by the known method.

Still an embodiment of the invention, the immunization in rabbits are carried out three times with purified coat protein of CVB and Freund's complete adjuvant in the ratio of 1:1 at weekly intervals.

Still in an another embodiment of the present invention, the route for immunization may be intramuscularly, subcutaneously or intravenously.

Yet in an another embodiment of the present invention, the rabbits are bled after 14 to 15 days to obtain polyclonal antibodies against CVB coat protein.

Yet in an another embodiment of the present invention, the polyclonal antibodies against CVB coat protein are purified from the serum by known methods.

Yet another embodiment of the present invention, the microtiter plates are coated with polyclonal antibodies diluting in a coating buffer in a ratio ranges from 1:500-1:1000 followed by 4-5 times washing with PBS-T.

Yet another embodiment of the present invention, the test samples are prepared in microtiter plates by macerating infected leaf tissue from plant with extraction buffer followed by dilution from 1×-1/150× of the original antigen.

Yet in another embodiment of the present invention, the microtiter plate is incubated overnight at about 37° C. followed by washing to allow coating of antigen in the wells.

Yet in an another embodiment of the present invention, the antibody conjugate in ECI buffer is added in the ratio ranges between 1:500 to 1:1000 for a period of about 2 hrs at about 37° C. followed by washing with PBS-T Yet in an another embodiment of the present invention, about 100 µl of about 1 mg/ml p-nitrophenyl phosphate solution in PNP buffer is added in the mix.

Yet in an another embodiment of the present invention, the reaction is terminated by adding about 50 µl of about 3M NaOH after 15-20 min to obtain yellow color product.

Yet in an another embodiment of the present invention, the color product is antigen and antibody conjugate.

Yet in an embodiment of the present invention, the absorbance of colored product is measured at 405 nm for detection of *Chrysanthemum virus* B (CVB).

Further, the present invention also provides a diagnostic kit useful for detection of coat protein of *Chrysanthemum virus* B (CVB) comprising:

a) polyclonal antibodies against *Chrysanthemum virus* B (CVB) coat protein in plants;

b) conjugate labeled with alkaline phosphatase;

c) coating buffer;

d) extraction buffer;

e) ECI buffer;

f) PNP buffer;

g) Instruction manual.

The following examples are given by way of illustration of the present invention and should not be construed to limit the scope of present invention.

Example 1

Detection of *Chrysanthemum Virus* B from Chrysanthemums

To check the activity of kit, different varieties of chrysanthemum were checked using DAS-ELISA. Samples were extracted in a similar fashion as described below in DAS-ELISA. At the same time they were also checked by a reference kit BIORAD (USA). The raised antibodies were tested against the newly discovered isolates including the isolates similar to Russian isolate reported earlier and found to detect effectively all the isolates. Reference kit showed weak reaction with other isolates while the antibody developed here showed a strong reaction with all isolates tested. The results are summarized in Table 1.

DAS-ELISA

1. Plates (Nunc Immuno TM plate, Denmark) were coated with 100 μl of polyclonal antibodies (diluted 1:10,000) in coating buffer and then incubated overnight at 4° C. in a humid box.
2. The plates were washed five times with PBS-T.
3. Antigen was prepared by macerating leaf tissue 1 g/2 ml in extraction buffer. Several dilutions were made corresponding to 1×-1/150× dilution of the original antigen and 100 μl of the diluted antigen was pipetted into wells of microtiter as per loading diagram and incubated at 37° C. for two hours in a humid box to allow coating of antigen in wells.
4. Washing steps were repeated and conjugate (diluted 1:500) in ECI buffer was added into the wells (100 μl/well). Plates were incubated for 2 hrs at 37° C. in a humid box.
5. After washing the plate with PBST, the wells were loaded with 100 μl solution of 1 mg/ml p-nitrophenyl phosphate made in PNP buffer (10% diethanolamine solution adjusted to pH9.8 with HCL).
6. After appropriate colour development (15-20 min), the reaction was terminated by adding 50 μl of 3M NaOH to each well.
7. Positive and negative controls were also made on the same plate. Absorbance at 405 nm was measured for complete ELISA plate with a flow ELISA micro plate reader. The reaction was considered positive if absorbance was observed to be greater than 0.1, which was three times of the negative control.

It reacted well with the positive sample, whereas negative in the negative control sample. The titration was found 1:10, 000.

Coating buffer: (0.05M per liter): 1.59 gm sodium carbonate and 2.93 gm sodium bicarbonate, pH 9.6

PBST buffer: 20 mM sodium phosphate pH 7.4; 150 mM NaCl and 0.05% (v/v) Tween 20. Extraction buffer: 1.3 g sodium sulphite (anhydrous), 20 g Polyvinylpyrrolidone (PVP) MW24-40,000, 0.2 g sodium azide, 2.0 g powdered egg albumin grade II and 20.0 g Tween-20 were dissolved in 1000 mlon 1XPBST and pH was adjusted 7.4.

ECI buffer: 2.0 g BSA, 20.0 g PVP 24-40,000 and 0.2 g sodium azide were dissolved in 1000 ml 1×PBST and pH adjusted to 7.4.

PNP buffer: 0.1 g magnesium chloride, 0.2 g sodium azide and 97 ml diethanolamine were dissolved in 800 ml distilled water and volume was made to 1000 ml and pH adjusted to 9.8.

| S. No | Variety | ELISA using Test Kit | ELISA using Reference Kit |
|---|---|---|---|
| 1. | Pink Gin | +++ | + |
| 2. | Funshine | ++ | + |
| 3. | Inga | + | + |
| 4. | Regol Time | +++ | + |
| 5. | Royal Mundial | + | + |
| 6. | Bronze Mundial | + | + |
| 7. | Otome Zakura | + | + |
| 8. | Tiching Queen | − | − |
| 9. | Mundial | ++ | + |
| 10. | Shymal | ++ | + |
| 11. | Chandrama | + | + |
| 12. | White Stafour | +++ | + |
| 13. | Fish Tail | + | + |
| 14. | Pancho | ++ | + |
| 15. | Akita | ++ | + |
| 16. | White Prolific | +++ | + |
| 17. | Pink Casket | +++ | + |
| 18. | Dignity | + | + |
| 19. | Jyoti | − | − |
| 20. | Penny Lane | + | + |
| 21. | Jubilee | ++ | + |
| 22. | Vasantika | ++ | + |
| 23. | Nanako | + | + |
| 24. | Kundan | + | + |
| 25. | Himani | +++ | + |
| 26. | Birbal Sahni | + | + |
| 27. | Jaya | + | + |
| 28. | Flirt | ++ | + |
| 29. | Lilith | − | − |
| 30. | Sharad Shobha | +++ | + |
| 31. | Megani | + | + |
| 32. | Jayanti | ++ | + |
| 33. | Niharika | ++ | + |
| 34. | Snow Ball | + | + |
| 35. | Meghdoot | − | − |
| 36. | White Shoesmith | ++ | + |

(−) = Negative reaction,
(+++) = Strong reaction,
(++) = Mild reaction,
(+) = Weak reaction

Example 2

Raising of Antisera

Purified recombinant coat protein was used an antigen for immunization of rabbit. Healthy white New Zealander male albino rabbits approximately six months old were used to raise the hyperimmune sera against CVB. Antigen (about 100 μg per injection) was mixed with Freund's adjuvant in the ratio of 1:1 and injected by two routes intramuscularly and sub-cutaneously into the thigh muscles of rabbits. First two injections were given along with Freund's complete adjuvant at the interval of one week. Similarly third and fourth injections were given along with Freund's incomplete adjuvant (1:1) at the interval of one week. After two-week immunization schedule, the animals were bled from the marginal ear vein. The blood was collected in a glass tube and allowed to clot at room temperature for an hour. Subsequently, glass tube containing clotted blood was kept at 4° C. overnight. The serum was collected using pasture pipette and centrifuged at 5000 rpm for ten min at 2-6° C. The supernatant was collected and stored at 4° C. after adding sodium azide to a concentration of 0.2% (w/v). To collect more serum, booster injections were given 5, 12, 16 and 22 weeks after the initial injection. For reference and serological testing, antiserum for CERV was procured from BioRad, USA.

Purification of Antibody

Separation of IgG from Whole Serum

A) By Ammonium Sulphate Precipitation:
 1. Distilled water (9 ml) was added to 1 ml of crude antiserum.
 2. Slowly drop wise 10 ml of neutralized saturated ammonium sulphate (Sigma) was added and continuously kept under stirring.
 3. After stirring, it was kept at room temperature for about 1 hour. The resulting solution should appear viscous and cloudy because of precipitation of antibodies i.e. IgG.
 4. Solution was centrifuged at 9000 g for 15 min and precipitate was washed with 2 ml of half-strength PBS. Washing step was repeated three times to remove the traces of ammonium sulphate.
 5. Finally precipitate was dissolved in 1 ml of half strength PBS.
 6. O.D. was measured at a wavelength of 280 nm.
 7. The antibodies were diluted in a way that final concentration became 1 mg/ml (O.D. reading 1.4=1 mg/ml).
 8. 1 ml aliquots along with 0.02% w/v sodium azide were stored at −20° C. for further use.
   PBS (100 ml): Na2HPO4.12H2O=5.8 gm; NaH2PO4.2H2O=1.0 gm; NaCl=8.76 gm.

B) By Affinity Chromatography:
 1. Protein A—sepharose (Sigma) was swelled and packed in a column.
 2. Column was washed with equilibration buffer.
 3. Serum was diluted and passed through the column with a regulated flow.
 4. Unbound proteins were washed with PBS until no more protein leaves the column (it was monitored by spectrophotometer).
 5. Bound protein (IgG) was eluted with the elution buffer.
 6. pH was neutralized with Tris HCl.
 7. Column was regenerated by washing alternatively with equilibration buffer and storage buffer. Then the column was stored in storage buffer at 4° C.
 8. Elute was dialyzed thrice against PBS and stored at −20° C. until used further.
   PBS (100 ml): Na2HPO4.12H2O=5.8 gm; NaH2PO4.2H2O=1.0 gm; NaCl=8.76 gm.
   Equilibration buffer (5×): Tris—0.05 M; NaCl—0.15 M, pH 8.6.
   Storage buffer: Na2HPO4-0.05 M; Thomersol—0.05%, pH 6.0
   Elution buffer: CH3COONa—0.05 M; NaCl—0.15 M, pH 4.5

Preparation of Antibody Enzyme Conjugate (Using Alkaline Phosphatase)

1. 1 mg of alkaline phosphatase (Sigma) was dissolved in 2 ml of purified antibodies.
2. Fresh gluteraldehyde (25% stock, Merck) was added to the solution in such a way to make the final concentration 0.05% and mixed well.
3. It was incubated at room temperature for 4 hrs. A faint brown colour was developed.
4. After 4 hrs, it was centrifuged at 9000 g for 20 min.
5. The precipitate was washed twice with half strength PBS and finally dissolved in 2 ml of half strength PBS.
6. Bovine serum albumin (BSA) to 5 mg/ml and sodium azide to 0.02% w/v were dissolved in it to enhance its self life. It was stored at 4° C. till further use.

Evaluation of Alkaline Phosphatase Conjugate:
 Activity of conjugate was checked by DAS-ELISA as described in the examples given in complete specifications of patent using known positive and negative samples and titrated too.

Example 6

Preparation of Kit for Detection of Coat Protein of *Chrysanthemum Virus* B (CVB)

Said kit is prepared by assembling following ingredients along with an instruction manual. The methodology to prepare the following ingredients has already been mention in previous examples. The kit comprising the following:
 a) polyclonal antibodies against *Chrysanthemum virus* B (CVB) coat protein in plants as claimed in claim 2;
 b) conjugate labeled with alkaline phosphatase;
 c) coating buffer;
 d) extraction buffer;
 e) ECI buffer;
 f) PNP buffer.
 g) Instruction manual.

Advantages:
 The main advantages of the present invention are:
 1. Chrysanthemum is among the top ten cut flower crop in domestic as well as in the international Floriculture Trade. Since it is severely gets affected by CVB that reduces its flower quality and yield and in order to develop the disease free propagating material and selection of healthy plants by using indigenous diagnostic kit are absolutely essential as it helps in the plant virus management.
 2. The kit being polyclonal in nature can detect all CVB strains.
 3. The kit can detect the CVB in different Chrysanthemum cultivars giving more strong reaction compared to the reference kit (Table 1).
 4. All the components of the kit can be stored at 4° C. without any appreciable loss in activity while few components of the reference kit need to be stored at −20° C.
 5. Purification of the expressed protein enhances the purity and continuous supply of antigen.
 6. This being an indigenous diagnostic kit, is cost effective too.
 7. The diagnostic kit developed can be used for screening the virus free tissue culture raised plants.
 8. The diagnostic kit developed can be used in understanding the disease epidemiology and disease forecasting of CVB.
 9. The diagnostic kit developed can be used for virus monitoring in vector and weeds.
 10. CVB diagnostic kit has an application in plant quarantine thus helping in export and import of Chrysanthemums.
 11. CVB diagnostic kit has an application in raising virus free Chrysanthemum nursery.

What is claimed is:

1. A method for detection of *Chrysanthemum virus B* (CVB) in plants, comprising the steps of:
   a) immunizing an animal with a recombinant CVB coat protein comprising the amino acid sequence of SEQ ID NO: 3, and isolating polyclonal antibodies against CVB;
   b) using the polyclonal antibodies in a direct antibody sandwich enzyme linked immunosorbent assay (DAS ELISA) to detect CVB in a plant sample.

2. A method for detection of *Chrysanthemum virus B* (CVB) in plants, comprising the steps of:
   a) amplifying a CVB coat protein coding sequence from a sample, using a forward primer consisting of the nucleotide sequence of SEQ ID NO: 1 and a reverse primer consisting of the nucleotide sequence of SEQ ID NO: 2, cloning said coat protein coding sequence into an expression vector, and producing a recombinant CVB coat protein by expression from said vector, wherein said recombinant CVB coat protein comprises the amino acid sequence of SEQ ID NO: 3;
   b) immunizing an animal with said recombinant CVB coat protein and isolating polyclonal antibodies against CVB;
   c) using the polyclonal antibodies in a direct antibody sandwich enzyme linked immunosorbent assay (DAS ELISA) to detect CVB in a plant sample.

3. The method of claim 2, wherein the CVB coat protein coding sequence is amplified from a Chrysanthemum plant.

4. The method of claim 2, wherein the expression vector is pGEX-2TK, and wherein *Escherichia coli* strain BL 21 is transformed with the vector for production of the recombinant protein.

5. The method of claim 2, wherein the expression of CVB coat protein is induced with 0.25-1 mM IPTG at about 25° C. for 3.5-4 hours.

6. The method of claim 2, wherein the recombinant coat protein produced in step (a) is purified.

7. The method of claim 6 or 1, wherein the immunization is performed by immunizing a rabbit four times with the recombinant coat protein and Freund's complete adjuvant at a ratio of 1:1 at weekly intervals.

8. The method of claim 2 or 1, wherein the immunization is by intramuscular, subcutaneous or intravenous route.

9. The method of claim 7, wherein the rabbits is bled after 14 to 15 days.

* * * * *

SEQUENCE LISTING

<160> NUMBER OF SEQ ID NOS: 3

<210> SEQ ID NO 1
<211> LENGTH: 27
<212> TYPE: DNA
<213> ORGANISM: Artificial
<220> FEATURE:
<223> OTHER INFORMATION: Upstream primer

<400> SEQUENCE: 1
atgcctccca aaccggcacc aggtgat                                    27

<210> SEQ ID NO 2
<211> LENGTH: 24
<212> TYPE: DNA
<213> ORGANISM: Artificial
<220> FEATURE:
<223> OTHER INFORMATION: Downstream primer

<400> SEQUENCE: 2
tttataatgt cttattattc gcat                                       24

<210> SEQ ID NO 3
<211> LENGTH: 315
<212> TYPE: PRT
<213> ORGANISM: Coat protein of CVB

<400> SEQUENCE: 3

```
Met Pro Pro Lys Pro Ala Pro Gly Asp Asn Glu Gly Asn Ala Ser Gly
1               5                   10                  15

Ser Thr Pro Thr Pro Ser Pro Pro His Pro Ala Arg Thr Ala Glu Glu
            20                  25                  30

Ala Arg Leu Arg Leu Ala Glu Met Glu Arg Glu Arg Glu Gln Glu Gln
        35                  40                  45

Ser Leu Glu Glu Met Asn Ser Asn Thr Pro Asp Asp Asp Ala Arg Asn
    50                  55                  60

Ile Ser Arg Leu Thr Gln Leu Ala Ala Leu Leu Arg Arg Glu Gln Thr
65                  70                  75                  80

Asn Val His Val Thr Asn Met Ala Leu Glu Ile Gly Arg Pro Ala Leu
                85                  90                  95

Gln Pro Pro Pro Asn Met Arg Gly Asp Pro Thr Asn Met Tyr Ser Gln
            100                 105                 110

Val Ser Thr Asp Phe Leu Trp Lys Ile Lys Pro Gln Arg Ile Ser Asn
        115                 120                 125

Asn Met Ala Thr Ser Glu Asp Met Val Lys Ile Gln Val Ala Leu Glu
    130                 135                 140

Gly Leu Gly Val Pro Thr Glu Ser Val Lys Glu Val Ile Ile Arg Leu
145                 150                 155                 160

Val Leu Asn Cys Ala Asn Thr Ser Ser Ser Val Tyr Gln Asp Pro Lys
                165                 170                 175

Gly Val Ile Glu Trp Asp Gly Ala Ile Ile Ala Asp Asp Val Val
            180                 185                 190

Gly Val Ile Asn Glu His Ser Thr Leu Arg Lys Val Cys Arg Leu Tyr
        195                 200                 205

Ala Ala Val Ala Trp Asn Tyr Met His Leu Gln Gln Thr Pro Pro Ser
    210                 215                 220

Asp Trp Ser Ala Met Gly Phe His Pro Asn Val Lys Tyr Ala Ala Phe
```

```
                    225                 230                 235                 240

Asp Phe Phe Asp Tyr Val Glu Asn Gly Ala Ala Ile Gly Pro Ser Gly
                245                 250                 255

Gly Ile Val Pro Lys Pro Thr Arg Ala Glu Tyr Val Ala Tyr Asn Thr
                260                 265                 270

Tyr Lys Met Leu Ala Leu Asn Lys Ala Asn Asn Asp Thr Phe Gly
                275                 280                 285

Asn Phe Asp Ser Ala Ile Thr Gly Gly Arg Gln Gly Pro Ala Ile His
                290                 295                 300

Asn Asn Leu Asn Asn Ala Asn Asn Lys Thr Leu
305                 310                 315
```